United States Patent [19]
Kao et al.

[11] Patent Number: 5,120,727
[45] Date of Patent: Jun. 9, 1992

[54] RAPAMYCIN DIMERS

[75] Inventors: Wenling Kao, Paoli, Pa.; Robert L. Vogel, Stratford, N.J.; John H. Musser, Alameda, Calif.

[73] Assignee: American Home Products Corporation, New York, N.Y.

[21] Appl. No.: 706,821

[22] Filed: May 29, 1991

[51] Int. Cl.$^5$ .................. C07D 491/06; A61K 31/395
[52] U.S. Cl. .................................. 514/183; 514/321; 540/456
[58] Field of Search ................ 540/456; 514/183, 321

[56]           References Cited
           U.S. PATENT DOCUMENTS
   3,929,992  12/1975  Sehgal et al. ...................... 424/122

OTHER PUBLICATIONS
Can. J. Physiol. Pharmacol. 55, 48 (1977).

Primary Examiner—Robert T. Bond
Attorney, Agent, or Firm—Walter Patton

[57]           ABSTRACT
A rapamycin dimer of general formula (1)

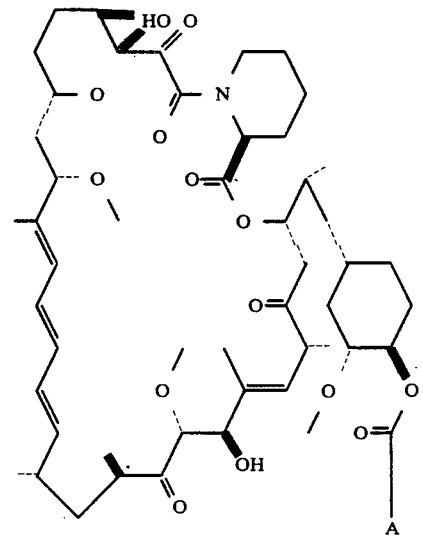

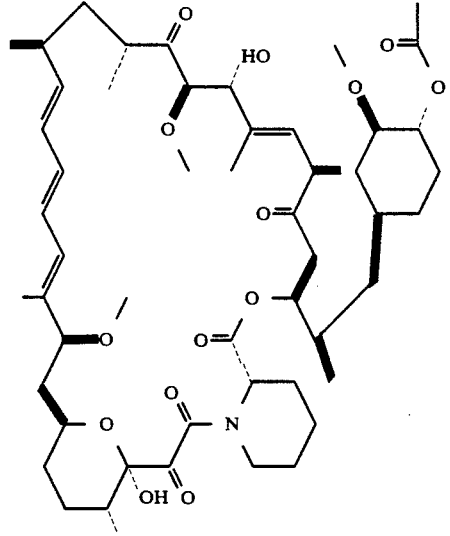

(I)

wherein
A is —(CH$_2$)$_n$—, —(CH$_2$)n—(CH=CH)—(CH$_2$)$_m$—,
—(CH$_2$)n—(—C≡C—)—(CH$_2$)$_m$—,

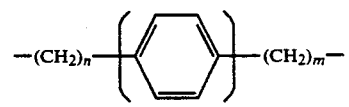

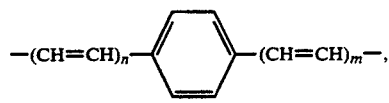

substituted alkyl, substituted alkenyl, substituted alkynyl, and substituted aromatic; n=1-10, m=1-10 and n=m or n≠m.

8 Claims, No Drawings or a pharmaceutically acceptable salt thereof, which is by virtue of its immunosuppressive activity is useful in treating transplantation rejection host vs. graft disease, autoimmune diseases, and diseases of inflammation.

RAPAMYCIN DIMERS

BACKGROUND OF THE INVENTION

This invention relates to rapamycin dimers of general formula (1), which possess immunosuppressive and/or antifungal and/or antitumor and/or anti-inflammatory activity in vivo and/or inhibit thymocyte proliferation in vitro and are therefore useful in the treatment of transplantation rejection, autoimmune diseases (i.e. lupus, rheumatoid arthritis, diabetes mellitus, multiple sclerosis), fungal infections (i.e. Candida albicans), cancer, and diseases of inflammation.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3,922,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1976) disclosed that rapamycin is effective in the experimental allergic encephalomyelitis model, a model for multiple sclerosis; in the adjuvant arthritis model, a model for rheumatoid arthritis; and effectively inhibited the formation of IGE-like antibodies.

The immunosuppressive effects of rapamycin have been disclosed in FASEB 3, 3411 (1989), rapamycin has been shown to be effective in inhibiting transplant rejection (U.S. patent application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978).

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions.

DESCRIPTION OF THE INVENTION

This invention relates to rapamycin dimers of general formula (1), which possess immunosuppressive and/or antifungal and/or antitumor and/or anti-inflammatory activity in vivo and/or inhibit thymocyte proliferation in vitro and are therefore useful in the treatment of transplantation rejection, autoimmune diseases (i.e. lupus, rheumatoid arthritis, diabetes mellitus, multiple sclerosis), fungal infections (i.e. Candida albicans), cancer, and diseases of inflammation.

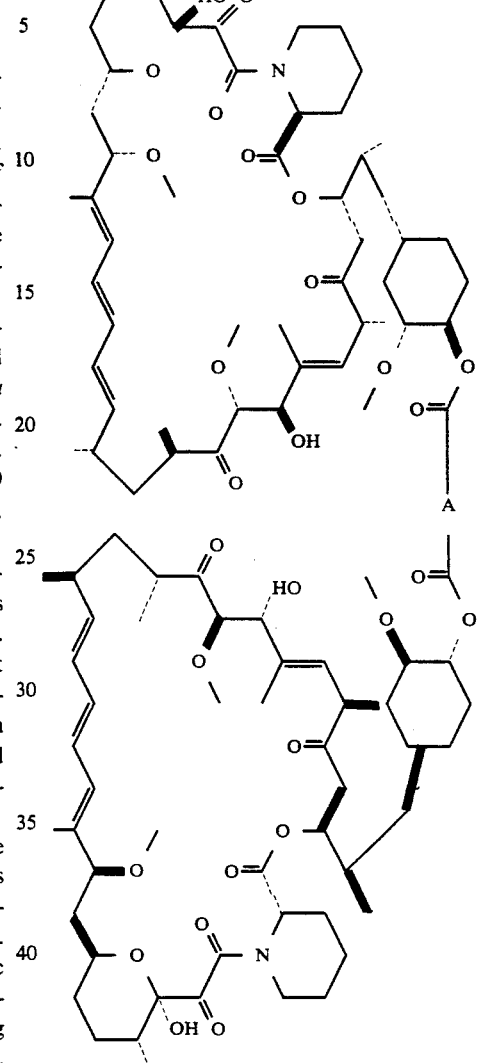

(I)

wherein

A is $-(CH_2)_n-$, $-(CH_2)_n-(CH=CH)-(CH_2)_m-$, $-(CH_2)_n-(-C\equiv C-)-(CH_2)_m-$,

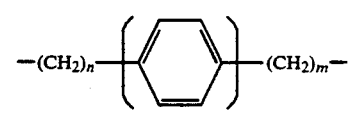

substituted alkyl, substituted alkenyl, substituted alkynyl, and substituted aromatic; $n=1-10$, $m=1-10$ and $n=m$ or $n\neq m$ or a pharmaceutically acceptable salt thereof.

The rapamycin dimers (1) of this invention can be prepared by standard literature procedure as outlined below

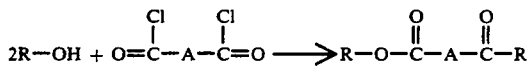

wherein R is rapamycin and A is as defined above.

PRIOR ART

The ester formation between alcohol and acyl halide has been described [Jerry March, Advanced Organic Chemistry, 3rd edition, published in 1985, page 346]. The specific reaction condition employed in this invention was developed by S. Rakhit of Ayerst Laboratories and reported in U.S. Pat. No. 4,316,885 (Feb. 23, 1982).

Immunosuppresive activity of the compounds of the present invention was evaluated in an in vitro standard pharmacological test procedure to measure lymphocyte proliferation (LAF).

The comitogen-induced thymocyte proliferation procedure (LAF) was used as an in vitro measure of the immunosuppressive effects of representative compounds. Briefly, cells from the thymus of normal BALB/c mice were cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio:

$$\frac{{}^3\text{H-control thymus cells} - \text{H}^3\text{-rapamycin-treated thymus cells}}{{}^3\text{H-control thymus cells} - \text{H}^3\text{-test compound-treated cells}}$$

The following table summarizes the results of representative compounds of this invention in this standard test procedure.

TABLE 1

| | Biological Activity - LAF Assay | | |
|---|---|---|---|
| | R/*A at 100 nM | at 10 nM | at IC$_{50}$ |
| Example 1 | 1.0 | 0.95 | — |
| Example 2 | 0.96 | 0.28 | — |
| Example 3 | 1.0 | 0.59 | — |
| Example 4 | 1.0 | 1.10 | 1.32 |

*Relative potency of analogs/rapamycin at dosages 100 nM and at 10 nM.

The results of this standard pharmacological test procedure for a representative compound of this invention demonstrates that the compounds of this invention are useful as immunosuppressive agents.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The following examples illustrate the preparation of representative compounds of this invention.

EXAMPLE 1

Rapamycin-42,42'-diester with hexanedioic acid

A solution of 0.13 g adipoyl chloride in 1 mL dry toluene was added dropwise at room temperature to a solution of 1.10 g rapamycin in 20 mL dry toluene and 2 mL dry pyridine; the resulting solution was heated at 50° C. under nitrogen with stirring for 65 hours. The product was extracted into ethyl acetate after addition of 20 mL 2N HCl and 20 mL brine. The ethyl acetate solution was dried over MgSO$_4$ and the solvent removed under reduced pressure. Chromatography through silica gel using 10% ethyl acetate in dichloromethane yielded 50 mg product as a yellow solid, mp 111°-142° C. IR (KBr): 3430, 2925, 1718, 1645, 1352, 1170, 785, and 632 cm$^{-1}$. NMR (CDCl$_3$, 400 MHz): δ 3.36 (s, 6H, OCH$_3$), 3.33 (s, 6H, OCH$_3$), 3.14 (s, 6H, OCH$_3$), 1.75 (s, 6H, CH$_3$), 1.65 (s, 6H, CH$_3$). MS (neg FAB): 1937, 590.

EXAMPLE 2

Rapamycin-42,42'-diester with heptanedioic acid

A solution of 0.25 g pimeloyl chloride in 1 mL toluene was added to a solution of 1.12 g rapamycin in 35 mL toluene and 2 mL pyridine; the resulting solution was heated at 50° C. for 44 hours under nitrogen with stirring. Upon cooling, 10 mL 2N HCl and 20 mL brine were added and the product was extracted into ethyl acetate (30 mL), which was washed with brine dried over MgSO$_4$ and evaporated. The residue was chromatographed through silica gel using a gradient of 5% to 30% ethyl acetate in dichloromethane, yielding 75 mg purified product as a pale yellow solid, mp 120°-150° C. IR (KBr): 3440, 2930, 1732, 1648 and 1455 cm$^{-1}$. NMR (CDCl$_3$, 400 MHz): δ 3.37 (s, 6H, OCH$_3$), 3.34 (s, 6H, OCH$_3$), 3.14 (s, 6H, OCH$_3$). MS (neg FAB): 1951, 590.

EXAMPLE 3

Rapamycin-42,42'-diester with octanedioic acid

A stirred solution of 1.24 g rapamycin and 0.30 g suberoyl chloride in 100 mL toluene and 2 mL pyridine was heated at 50° C. for 66 hours under nitrogen, then cooled, diluted with 100 mL ethyl acetate and treated with 20 mL 2N HCl and 50 mL brine. The organic portion was washed with brine, dried over MgSO$_4$, stripped of solvent, and chromatographed through silica gel using a gradient of 0.5% to 20% methanol in dichloromethane, yielding 140 mg product as a pale yellow solid, mp 117°-134° C. IR (KBr): 3430, 2920, 1728, 1640, 1442 and 980 cm$^{-1}$. NMR (CDCl$_3$, 400 MHz): δ 3.37 (s, 6H, OMe), 3.33 (s, 6H, OMe), 3.14 (s, 6H, OMe). MS (neg FAB): 1965, 590.

EXAMPLE 4

Rapamycin-42,42'-diacid with nonanedioic acid

A solution of 1.27 rapamycin and 50 mg azelaoyl chloride in 125 mL toluene and 2 mL pyridine was stirred at 50° C. under nitrogen for 65 hours, then cooled and treated with 20 mL 2N HCl. The organic portion was washed with brine, dried over MgSO$_4$, stripped of solvent, and chromatographed through silica gel using a gradient of 0.5% to 10% methanol in dichloromethane, yielding 110 mg product as a pale yellow solid, mp 107°-125° C. IR (KBr): 3450, 2935, 1730, 1650, 1455, 1100 and 990 cm$^{-1}$. NMR (CDCl$_3$, 400 MHz): δ 3.375 (s, 6H, OMe), 3.33 (s, 6H, OMe), 3.14 (s, 6H, OMe). MS (neg FAB): 1979, 590.

EXAMPLE 5

Rapamycin 42,42'-diester with 1,4-phenylenediacrylic acid

A solution of 100 mg 1,4-phenylenediacrylic acid in 5 mL thionyl chloride was heated at reflux under nitrogen for two hours. The thionyl chloride was removed under reduced pressure; the residue was dissolved in 5 mL toluene, added to a stirred solution of 0.90 g rapamycin in 25 mL toluene and 2 mL pyridine, and heated at 50° C. for 72 hours. The cooled reaction mixture was treated with 20 mL 2N HCl and diluted with 20 mL ethyl acetate and 50 mL brine. The product was extracted into ethyl acetate and chromatographed through silica gel using a gradient of 0 to 3 percent methanol in dichloromethane, yielding 60 mg product as a pale yellow solid, mp 121°-131° C. IR(KBr): 3420, 2930, 1715, 1640, 1445, 1100 and 980 cm$^{-1}$. NMR (CDCl$_3$, 400 MHz): δ 7.64 (d, 2H, J=12.0 Hz), 7.52 (s, 4H, aromatic), 6.47 (d, 2H, J=12.0 Hz), 3.38 (s, 6H, OMe), 3.32 (s, 6H, OMe), 3.12 (s, 6H, OMe). MS (neg FAB): 2009 (M$^-$), 1112, 590.

What is claimed is:

1. A rapamycin dimer of formula (1)

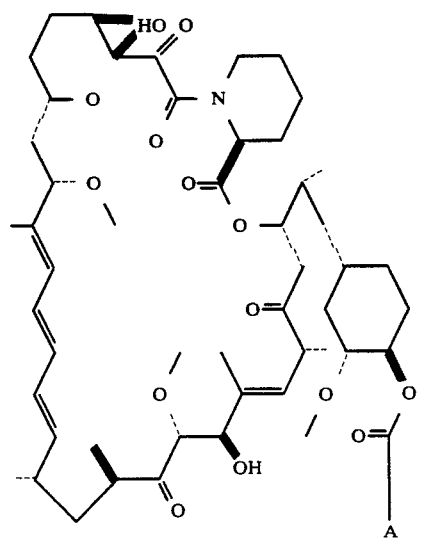

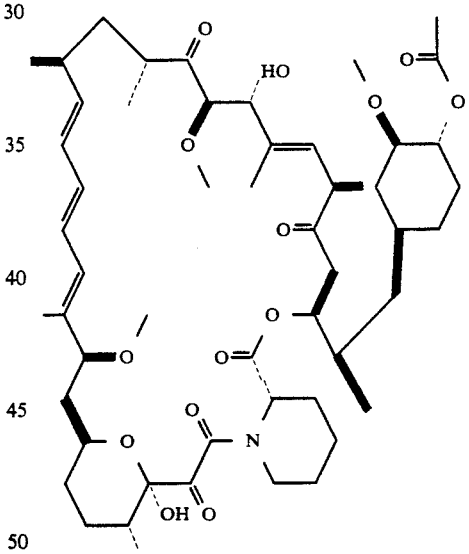

wherein
A is —(CH$_2$)$_n$—, —(CH$_2$)$_n$—(CH=CH)—(CH$_2$)$_m$—,
—(CH$_2$)$_n$—(—C≡C—)—(CH$_2$)$_m$—,

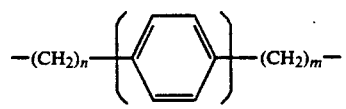

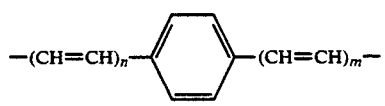

n=1-10, m=1-10 and n=m or n≠m
or a pharmaceutically acceptable salt thereof.

2. A compound of claim 1 wherein A is -(CH₂)₄- or a pharmaceutically acceptable salt thereof.

3. A compound of claim 1 wherein A is -(CH₂)₅- or a pharmaceutically acceptable salt thereof.

4. A compound of claim 1 wherein A is -(CH₂)₆- or a pharmaceutically acceptable salt thereof.

5. A compound of claim 1 wherein A is -(CH₂)₇- or a pharmaceutically acceptable salt thereof.

6. A compound of claim 1 wherein A is

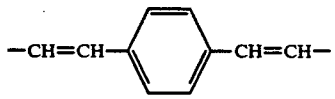

or a pharmaceutically acceptable salt thereof.

7. A method of treating transplantation rejection, host vs. graft disease, autoimmune diseases, and diseases of inflammation in a mammal by administering an effective amount of a compound which is a rapamycin dimer of formula (1)

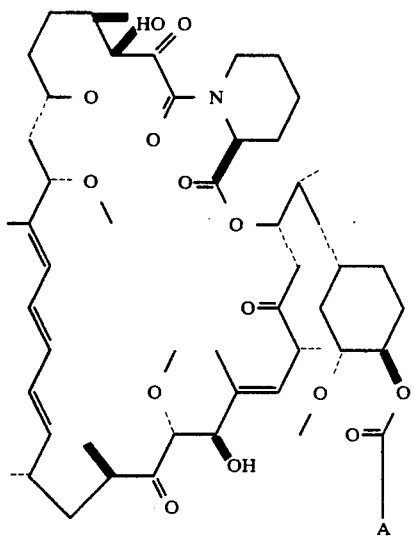
(I)

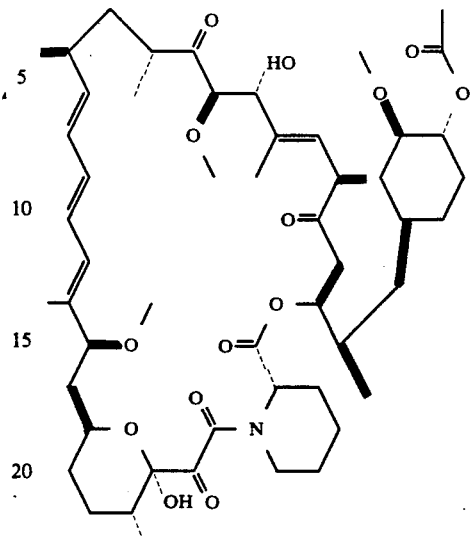
-continued wherein
A is —(CH₂)$_n$—, —(CH₂)n—(CH=CH)—(CH₂)$_m$—, —(CH₂)n—(—C≡C—)—(CH₂)$_m$—,

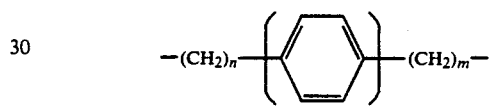

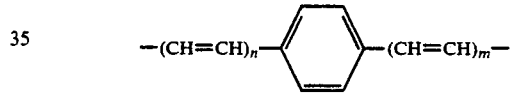

n=1-10, m=1-10 and n=m or n≠m.

8. A pharmaceutical composition useful for treating transplantation rejection, host vs. graft disease, autoimmune diseases, and diseases of inflammation in a mammal comprising an effective amount of a compound of claim 1 or a pharmaceutically acceptable salt thereof and a pharmaceutically acceptable carrier.

* * * * *